United States Patent
Bowen

(10) Patent No.: US 9,211,351 B2
(45) Date of Patent: Dec. 15, 2015

(54) METHODS FOR VARIABLY STERILIZING AQUEOUS LIQUIDS

(76) Inventor: John G. Bowen, Prescott, AZ (US)

(*) Notice: Subject to any disclaimer, the term of this patent is extended or adjusted under 35 U.S.C. 154(b) by 635 days.

(21) Appl. No.: 13/136,446

(22) Filed: Aug. 1, 2011

(65) Prior Publication Data

US 2011/0290739 A1 Dec. 1, 2011

Related U.S. Application Data

(60) Continuation-in-part of application No. 12/925,912, filed on Nov. 2, 2010, now abandoned, which is a division of application No. 12/799,932, filed on May 5, 2010, now Pat. No. 7,862,784, which is a continuation of application No. 12/008,038, filed on Jan. 8, 2008, now abandoned, which is a continuation-in-part of application No. 11/210,217, filed on Aug. 22, 2005, now abandoned.

(51) Int. Cl.
| | |
|---|---|
| C02F 1/00 | (2006.01) |
| C02F 1/02 | (2006.01) |
| A23L 3/16 | (2006.01) |
| A61L 2/04 | (2006.01) |
| A61L 2/28 | (2006.01) |

(52) U.S. Cl.
CPC ... *A61L 2/04* (2013.01); *A61L 2/28* (2013.01); *C02F 1/006* (2013.01); *C02F 1/02* (2013.01); *C02F 2209/02* (2013.01); *C02F 2209/03* (2013.01); *C02F 2209/40* (2013.01); *C02F 2301/04* (2013.01); *C02F 2303/04* (2013.01); *Y02W 10/37* (2015.05)

(58) Field of Classification Search
None
See application file for complete search history.

(56) References Cited

U.S. PATENT DOCUMENTS

| | | | | |
|---|---|---|---|---|
| 5,403,564 | A * | 4/1995 | Katschnig et al. | 422/307 |
| 5,647,986 | A * | 7/1997 | Nawathe et al. | 210/608 |
| 5,667,828 | A * | 9/1997 | Nikdel et al. | 426/231 |
| 2005/0063885 | A1 * | 3/2005 | Katschnig et al. | 422/307 |
| 2006/0041248 | A1 * | 2/2006 | Patton et al. | 604/890.1 |

* cited by examiner

*Primary Examiner* — Nam Nguyen
*Assistant Examiner* — Richard Gurtowski

(57) ABSTRACT

A method for flow-through aqueous liquid sterilization which employs apparatus operating at substantially fixed temperatures and pressures and variable flow rates through the apparatus for controllably processing aqueous liquids to achieve predetermined values of Sterility Assurance Levels (SAL's).

2 Claims, 2 Drawing Sheets

METHODS FOR VARIABLY STERILIZING AQUEOUS LIQUIDS

CONTINUATION

This U.S. Patent Application is a Continuation-in-Part of U.S. patent application Ser. No. 12/925,912, filed Nov. 2, 2010, which is a Division of U.S. patent application Ser. No. 12/799,932 filed May 5, 2010, now U.S. Pat. No. 7,862,784 B2, which is a Continuation of a U.S. patent application Ser. No. 12/008,038, filed Jan. 8, 2008 (now abandoned), which is a Continuation-in-Part of U.S. patent application Ser. No. 11/210,217, filed Aug. 22, 2005 (now abandoned), by John G. Bowen, all titled, APPARATUS AND METHODS FOR VARIABLY STERILIZING AQUEOUS LIQUIDS.

FIELD OF INVENTION

This invention relates to methods by which aqueous (water based) liquids are decontaminated, collected and stored for culinary purposes. This invention is further related to methods which decontaminate such aqueous liquids without use of chemical or light energy processes.

BACKGROUND OF THE INVENTION

There is an ever increasing need for new, more effective, efficient and lower cost methods for decontaminating water and other water based (aqueous) liquids. As and example, Center for Disease Control and Prevention (CDC) reports in a Mar. 6, 2003, report on BACTERIAL WATERBORNE DISEASES that each year there are 3.5 billion episodes of illness and a resulting three million estimated deaths caused by contaminated water and despite global efforts improvements have barely kept pace with population increases. From an Emerging Infectious Diseases article, dated 10 Oct. 2005, it was reported that seventeen percent of all deaths of children under five years of age in the developing world was caused by contaminated water. With these statistics, it is astounding that no water purification method is currently available and in-use to prevent such water borne illnesses. Likely such is not available due expense of currently available water purification systems. The simplicity and associated potential low cost of manufacture and operation of devices made according to the instant invention promise to make substantial in-roads toward a solution to these problems. As an example, a gallon of sterile water from this instant invention can be produced at an expense of approximately two hundred watt hours of energy.

A profound example of changes in methods of water purification is a new water treatment plant located in Salt Lake City, Utah. Rather than chlorine, this plant employs ozone and ultraviolet light, as ultraviolet light is more effective than chlorine in terms of decontaminating water containing cryptosporidium and other chlorine resistant microbes. However, use of light is known to sometimes be ineffective and at other times be unpredictable when used in water that has variable light transmission quality.

While decontamination and purification are terms generally considered in an ultimate context of complete elimination of any and all undesirable contaminants, it is generally known, as disclosed on page 68 of *Principles and Methods of Sterilization, 2$^{nd}$ Edition*, published by Charles C. Thomas, Springfield, Ill., in 1983, that complete sterilization should never be considered as completely attained. Rather, biological contaminants should be considered to be eliminated logarithmically, such as being measured by time constants dependent upon intensity and method of treatment. As an example, if a process, using heat at a specific temperature, kills a particular organism at a rate of 90% per minute, 10% of the organism survives at the end of the first minute of treatment. One percent survives the second minute of treatment and to achieve a kill of 99.9999% requires a treatment period of six minutes. Thus, at a constant temperature (constant application of heat) kill rate becomes a function of time.

To codify a standard for sterilization, the Association for the Advancement of Medical Instrumentation (AAMI), 110 N. Glebe Road, Suite 220, Arlington, Va. 22201-4795 has issued a proposed standard for selecting appropriate Sterility Assurance Levels (SAL's) (See *Proposed Standard on Selecting Appropriate Sterility Assurance Levels* published as an Internet bulletin on Feb. 10, 2000). While, SAL's are generally used to determine levels of sterilization for medical products, a similar standard may be considered for water and other aqueous liquid purification, as well. AAMI reports, as examples, that items which come into contact with skin may need only an SAL of $10^{-3}$ while implants or sterile liquid pathway products should be sterilized to an SAL of $10^{-6}$.

Similar considerations might be applied to water purification. Drinking water from one source might be sufficiently pure at an SAL of $10^{-3}$ while another source might require an SAL of $10^{-4}$ or better. It may also be desired to have a single water purification or sterilization system which could be used for various purposes (e.g. for drinking water or for a medical application). Also, such aqueous liquids as milk might require different sterilization for different packaging and storage requirements. This invention is meant to fulfill a variety of applications related to meeting requirements for a variety of sterilization levels.

A number of U.S. Patents and Patent Applications cite methods and apparatus for achieving various levels of sterilization of aqueous liquids. An example of such a patent is provided by U.S. Pat. No. 6,136,362, issued Oct. 24, 2000, to Roger J. Ashton (Ashton), titled HIGH TEMPERATURE/ SHORT TIME PASTEURIZATION SYSTEM AND METHOD OF CLEANING. Ashton particularly teaches a way of cleaning a system used for pasteurization of milk. While pasteurization has long been used to improve safety and lengthen term for storage of milk, pasteurized milk has also been recognized as still containing microbes and, therefore, is not completely sterilized. Even so, continuous flow pasteurization is not taught in Ashton, but rather Ashton teaches a system for cleaning a pasteurization circuit without connecting and disconnecting apparatus. Also, Ashton does not teach regulating pressure at a temperature required for sterilization.

Another U.S. Pat. No. 5,403,564 issued Apr. 4, 1995 to Helmut Katschnig et al. (Ketschnig 564), titled APPARATUS FOR HEATING AND THERMAL DECONTAMINATING A PUMPABLE OR POURABLE MATERIAL, discloses apparatus for heating and thermal decontamination using a microwave unit. As such, Katschnig makes no attempt to insure that non-sterile material will not contaminate a conduit leading from the microwave unit to a discharge tube. In other words, Katschnig sterilizes by means of radiation and assures any achieved sterilization only within the zone of radiation.

In a U.S. Patent Application, Publication Number 2005/ 0063885 A1, Katschnig et al. (Katschnig 885), filed September 2004, discloses a system and method for sterilizing and pasteurizing pumpable or free flowing medium. In paragraph [0019] Katschnig 885 relates, "The apparatus operates as follows: When starting the apparatus, incoming contaminated medium is circulated by pump 4 to flow from the storage tank 2 via the heating unit 5, temperature holding device 6, conduit branch 13, pump 7 and shut-off member 16 back to storage tank 2." It is noted with concern that such a start up results in contaminated medium flowing through a common pathway 24 which leads to conduit branch 13 back to storage tank 2 and to conduit branch 14 which provides the effluent pathway. Such a problem resulting from a bifurcated pathway is not possible using a method which employs no bifurcation and only releases sterilized matter after treatment at a predetermined temperature and pressure for a predetermined period of time, which is the case of the instant invention.

A U.S. Pat. No. 6,673,311 B1 issued Jan. 6, 2004, to Kazuyoshi Sotoyama, et al., (Sotoyama) titled METHOD AND APPARATUS FOR CONTINUOUS HEAT STERILIZATION OF LIQUID, discloses sterilization by heating and rapid release of pressure. As such, Sotoyama employs a rapid high pressure release (which may be a pressure drop in the range of 2 to 100 MPa). Such an initial pressure is much higher than pressure employed in the instant invention which is in the range of 0.2 to 0.5 MPa, and no rapid pressure release is employed in the instant invention.

U.S. Pat. No. 6,579,494 B1 issued Jun. 17, 2003, to Jacques Chevallet, et al. (Chavallet) and titled PROCESS AND DEVICE FOR STERILIZING AND DISPENSING A LIQUID FOR MEDICAL USE discloses method and apparatus for sterilizing liquids for medical use. As such, Chavellet discloses and claims a validating structure which permits and requires a "means for validating a sterilization treatment" resulting from an implemented adjustable heating apparatus. Chevallet makes an interesting point relative to checking a $10^{-6}$ level of viable microorganisms in a continuous flow apparatus, saying that such a check according to Poisson probability is unachievable. For this reason, processes according to the present invention necessarily rely upon fixing at least two parameters (temperature and pressure) and post delivery validation testing.

BRIEF SUMMARY AND OBJECTS OF THE INVENTION

In brief summary, this novel invention alleviates all of the known problems related to safely and efficaciously decontaminating aqueous liquids for a variety of uses. The invention is a "flow-through" device which receives influent contaminated liquid or impure liquid of questionable pollution and provides a sterilized effluent product decontaminated to meet a variety of applications. Further, sterilization levels (i.e. SAL's) may be facilely, accurately, predictively and variably controlled, depending upon known or assumed characteristics of an influent liquid to be sterilized and projected use of that liquid. Sterilization to various levels is realized through changing but a single variable (flow rate through the apparatus) and while other parameters, such as heating temperature, pressure, etc., are kept substantially constant.

The invention comprises methods associated with a liquid source and a flow regulation controller which provide a variable control setting for flow of influent liquid. Further, an optional input pump provides sufficient pressure to the source to open a pressure sensitive valve (used if upstream source pressure is inadequate to open the pressure sensitive valve). From the source, liquid is distributed via closed reservoir (e.g. coils) within a heating chamber.

The heating chamber employs a non-linear heat-sink material which provides controlled heating at a substantially constant temperature. It is important within the inventive processes associated with these methods that temperature be kept constant to assure a predictable organism kill rate within liquid flowing through the reservoir. (For example, for a predictable organism kill rate, temperature should be kept substantially constant, as in an embodiment of the instant invention, controlled within plus or minus three degrees Centigrade.) The reservoir should have a capacity for holding a liquid volume at least equal to a given maximum desired flow rate for a time necessary for sterilizing the liquid to a predetermined SAL value.

Strategically disposed in thermal communication with the reservoir, a temperature sensor is used to assure that liquid flowing through the heating chamber is at least at a temperature which is consistent with desired sterilization. Of course, the controlled flow rate determines effective dwell time in the heating chamber and, therefore, an ultimate SAL value of effluent liquid streaming from the reservoir.

Heating of the heating chamber may be performed by such heat sources as electric elements, gas burners, solar and/or geothermal energy. To assure that heating is sufficiently accurately controlled, it is preferred that the heating chamber provide an accurately controlled temperature "bath" through which the liquid flows. Preferably, that bath is filled with a paraffin having a predetermined melting temperature, thereby employed to maintain the precise temperature.

Actual sterilization efficiency is dependent upon maintaining a liquid temperature above 100° Centigrade (e.g. 150° Centigrade) at a pressure (e.g. 55 psi) which assures achieving a desired SAL as liquid flows for a predetermined time through the reservoir. Thus, maintaining a predetermined flow rate is the primary and singular variable used to achieve a target SAL.

Other than flow control at the source or influent site of the reservoir, two other flow control elements are employed. Downstream, near the effluent site of the reservoir, a pressure relief valve (earlier referenced) is disposed in the effluent flow path to guarantee that a predetermined minimum upstream pressure is maintained within the reservoir. Another, second, valve is also serially disposed in the flow path, preferably distal from the heating chamber and the pressure release valve.

The second valve may selectively be gated by an "AND" combination of water temperature and pressure sensors, although a temperature regulated valve in series with the first valve also performs the "AND" function. The temperature and pressure sensors are each disposed at individual predetermined strategic sites within the water flow path. In one embodiment, temperature is sensed by a bi-metallic sensor switch disposed within the reservoir, sufficiently close to the influent site of the reservoir to assure that a predetermined minimum sterilization temperature has been achieved, thereby assuring maintenance of the minimum sterilization temperature within the remainder of the reservoir. In this embodiment, a pressure sensor, having a pressure-sensitive switch, is disposed downstream from the reservoir. The pressure sensor is selectively closed when a predetermined sterilization upstream pressure is detected. The contacts of the temperature sensor and pressure sensor are connected in series such that when contacts of each switch close the second valve is opened (i.e. before the second valve opens, the temperature sensor must sense at least a predetermined temperature and the pressure sensor, likewise, must have detected a predetermined pressure.) Importantly, simultaneously meeting these combined conditions assures achieving target SAL in the effluent, thereby protecting sterility of the downstream system.

Also, each switch of each sensor is opened and closed at different values (of temperature and pressure), thereby creating a hysteresis in each switching parameter and, as a result, assuring stable operation. For example, the temperature sensor may operate to close the temperature switch at a temperature of substantially 150° C. and operate to open the switch at 140° C. In tandem with the temperature sensor, the pressure sensor may operate to close the pressure switch at 50 psi and open the pressure switch at 40 psi. In the case of the "AND" gate, only when both switches are closed is the second valve opened.

To preserve as much energy as possible, it is preferred to steer effluent through a heat exchanger which transfers heat from the effluent to the influent such that temperature, and therefore thermal energy, of liquid flowing from the reservoir is substantially reduced. In this manner, by controlling dwell time in the reservoir by controlling liquid flow within predetermined limits, liquid of a desired SAL is provided as a cooled continuous flow effluent product. It is also important that all liquid remains in a liquid state through the entire flow path.

The invention aims to provide a method by which an aqueous liquid influent, contaminated by microbes, is sterilized to a predetermined SAL, said method comprising the steps of:
  establishing a substantially fixed, predetermined anti-microbial temperature;
  establishing a pressure correlated to the fixed temperature at a closed flow-through system which is otherwise free of all other sources of contamination;
  displacing at a preset flow-rate, the microbe containing influent liquid into the closed flow-through system, that flow-rate being correlated to the substantially fixed values of temperature and pressure;
  imposing the established temperature, pressure and preset flow-rate conditions upon the aqueous liquid as it is displaced through the system without use of radiation causing microbes to be killed thereby producing water which is free of vaporization and sterilized to a predetermined SAL;
  preventing subsequent introduction of microbes into the aqueous liquid being treated for sterilization to the predetermined SAL; and discharging the aqueous liquid as a non-radiated effluent from the system.

Further, the invention aims to provide a method by which an influent aqueous liquid containing microbes is sterilized to a predetermined SAL in a closed system and discharged from the closed system as a so treated effluent comprising the steps of:
  providing a closed flow-through system free of microwave radiation wherein the only source of contamination is the microbe-containing influent aqueous liquid;
  controlling the system to achieve start-up of the system by preventing flow in the system while collectively elevating temperature and pressure conditions within the system to predetermined substantially fixed levels effective for sterilizing the influent aqueous liquid to be free of living organisms to a predetermined SAL;
  after non-flow temperature and pressure levels have been reached within the system, controlling the system to achieve into and through the system a unidirectional flow-rate of each unit volume of the aqueous liquid while retaining the substantially fixed temperature and pressure conditions within the system such that each unit volume of aqueous liquid is resident within retained temperature and pressure conditions for a sufficient period to be stabilized.

Accordingly, it is a primary object to provide an efficacious method of aqueous liquid purification system which controllably sterilizes aqueous liquid to a predetermined SAL.

It is a fundamental object to provide an aqueous liquid purification method which controllably sterilizes an aqueous liquid to a predetermined SAL by controlling rate of flow of the aqueous liquid through said system.

It is an important object to provide a method which inherently maintains a substantially fixed predetermined pressure in a heating unit thereby assuring that aqueous liquid in the heating unit is maintained in a liquid state while being sterilized therein.

It is an object to provide a process by which a heating unit, through which aqueous liquid flows and in which the aqueous liquid is heated, is maintained at a substantially fixed temperature.

It is an object to provide a system which assures a predetermined pressure of effluent flowing from said system.

It is an object to provide an energy efficient system which transfers thermal energy from effluent liquid, after sterilization, to influent liquid before sterilization, thereby reducing effluent temperature to a predetermined lower temperature level before leaving the system and preheats influent aqueous liquid before it enters the heating unit.

It is a very important object to sterilize an aqueous solution to an SAL of $10^{-6}$ at an energy cost not greater than 200 watt-hours per gallon.

These and other objects and features of the present invention will be apparent from the detailed description taken with reference to accompanying drawings.

DETAILED DESCRIPTION OF THE ILLUSTRATED EMBODIMENTS

In this description, the term proximal is used to indicate nearness of a referenced item to the object of the sentence describing its position. The term distal should be interpreted as indicating "away from" a referenced item. Numbers and primes of the same numbers are used to indicate items of related mechanics and function, but which may have physical differences.

Figure 1:
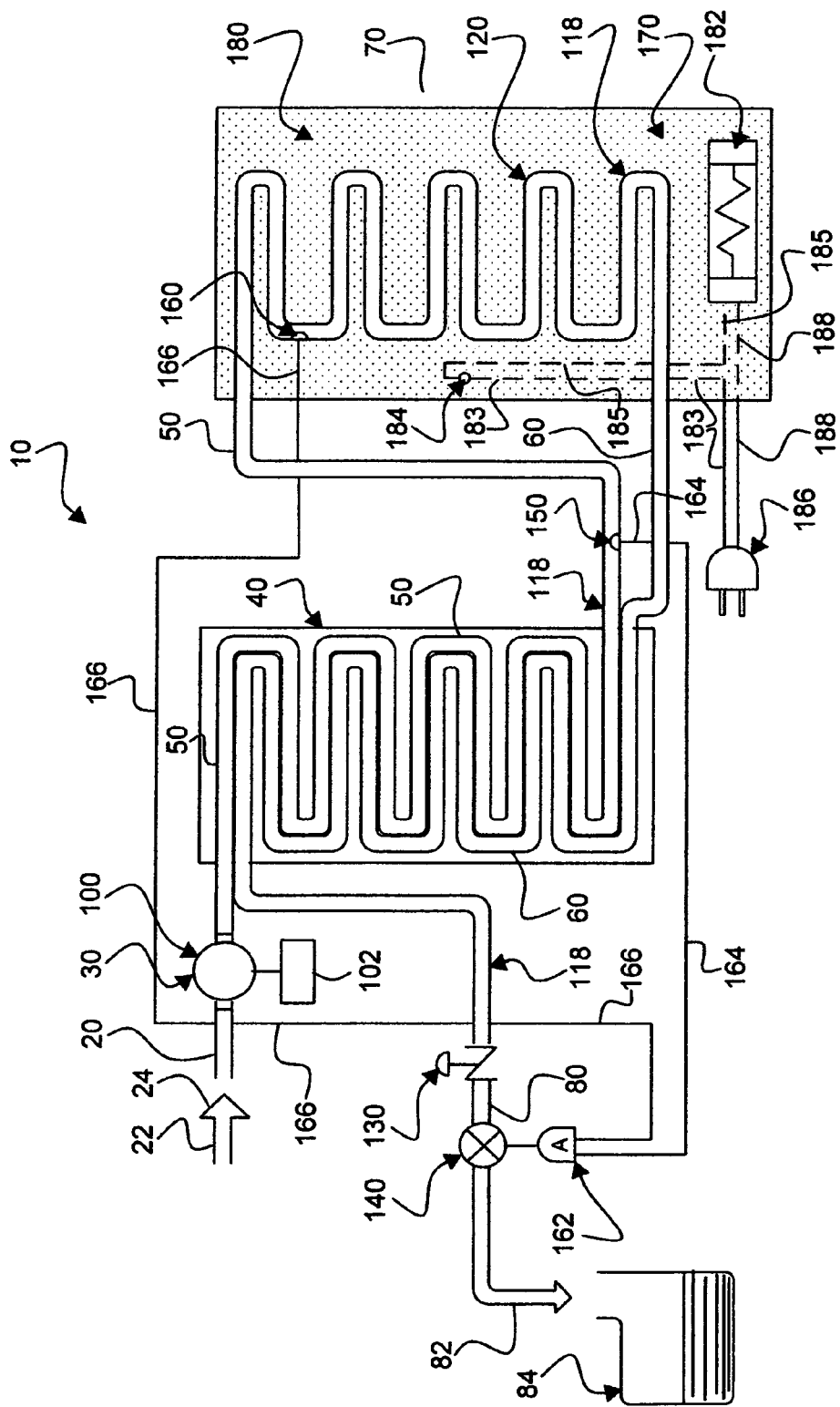
FIG. 1 is schematic of an aqueous liquid sterilization system which may be adjusted to control degree of purification (SAL).

Reference is now made to the embodiment illustrated in FIG. 1. While only a single embodiment and associated method is provided herein, it should be apparent to one skilled in water and other aqueous liquid purification by sterilization that other embodiments and methods may be employed within the scope of the invention.

As seen in FIG. 1, a water sterilization system 10 comprises an influent channel 20, wherethrough water from a source 22 (see arrow 24) is delivered, a flow controller subsystem 30, a heat exchanger 40 through which influent liquid flows in an input pathway 50 and through which effluent liquid flows in an output pathway 60, a heating chamber 70 and a discharge pathway 80 (see arrow 82). Pathway 80 may often lead to a container (seen in FIG. 1 as container 84). Note that all flow in system 10 is unidirectional, keeping parts distal from heating chamber 70 (i.e. parts associated with discharge pathway 80) uncontaminated by flow reflux in a direction opposite arrow 82.

Flow controller subsystem 30 may comprise a pump 100 and a pump controller 102. Pump 100 should have a variable pumping capacity to supply a predetermined volume of liquid flow through the system against a back pressure which is the consequence of a temperature rise in heating chamber 70 and back-pressure of release valve 130. It should be noted that no pump may be required if hydrostatic pressure of the source 22 exceeds the back pressure of valve 130. However, in any case, it is necessary for flow to be controlled to assure liquid is retained in heating chamber 70 for a period sufficiently long to achieve a desired SAL. In cases where flow is not pump controlled and upstream pressure is known, a flow restricting orifice (not shown) may be employed. In this instant invention because controlled flow rates are used to variably determine SAL's of effluent, an adjustable orifice (also not shown) may be employed.

Heat exchanger technology is well known in water heating and cooling art. However, it is important that as much energy as possible be transferred from liquid in output or effluent pathway 60 to input or influent pathway 50 within heat exchanger 40 to minimize heat energy loss. For these reasons, pathway 50 should be proximal to and in good thermal communication with pathway 60.

It is critical that the system liquid pathway 118 (a combination of input pathway 50, an internal heating chamber pathway 120 and output pathway 60 be capable of withstanding an internal pressure generated by heating of liquid within the pathway to a desired temperature while maintaining fluid therein in a liquid state. As an example, liquid at 150° Centigrade has a vapor pressure of 55 pounds per square inch (psi). To assure liquid at 150° does not change state, internal pressure in pathway 118 must exceed 55 psi.

For this reason, a flow resisting element, such as a pop valve 130 is serially connected in a section of output pathway 60 distal from heating chamber 70 and heat exchanger 40. Pop valve 130 is selected to open at a first higher pressure level and close at a second lower pressure level. The difference between the higher pressure level and lower pressure level being a defined operating pressure differential wherein liquid in pathway 120 is sterilized over a predetermined period of time. As this pressure differential of a pop valve is considered to control pressure over a relatively small differential, the pressure, so controlled, is considered to be fixed.

To further assure that there is no flow through pathway 118 (and discharge pathway 80) until conditions for water sterilization have been reached in pathway 120, a second valve, numbered 140, is serially connected in discharge pathway 80. In FIG. 1, valve 140 is seen to be a solenoid valve activated by an AND combination of two switches, a pressure sensor switch 150 and a temperature sensor switch 160.

Interestingly, it may be noted that the pressure sensing by valve 130, as a back pressure regulator, performs substantially the same pressure controls as that resulting from activity of sensor 150. Thus, action of pressure sensor 150 is redundant and AND gate 162 with input 164 may be eliminated, and output of temperature sensor 160 used to directly control valve 140.

Note, that in this case, the serial disposition of valves 130 and 140 provide a logical "AND" combination, eliminating the need for AND gate 162.

Sensor switch 160 activates to open at or below a first lower predetermined temperature level of liquid in pathway 120 and to close at a second higher predetermined level in pathway 120. It should be noted that heating of chamber 70 is controlled by another sensor (184 as disclosed in detail hereafter).

Similarly, pressure sensor switch 150 activates to open at a third predetermined lower pressure level (which is substantially the same as the first pressure level disclosed supra) and closes at a fourth higher pressure level (which is substantially the same as the second higher pressure level disclosed supra).

As an example, pressure sensor switch 150 may be selected to close at 80 psi and open at 55 psi, while temperature sensor switch 160 may close at 150° centigrade and open at 140° centigrade. As such, switch 150 must sense 80 psi and switch 160 must sense 150° centigrade (symbolized by AND gate 162) to open valve 140 to permit effluent to flow through system 10 (with valve 130 also open). Note, pressure sensor switch 150 is connected to AND gate 162 via line 164 and temperature sensor switch 160 is connected to AND gate 162 via line 166.

To sterilize water at least to a predictable SAL, both system 10 water flow rate and heating chamber 70 temperature must be known and well controlled to assure liquid in pathway 120 is resident in heating chamber 70 for a long enough period to assure the desired sterilization level. Water flow rate is closely controlled by pump 100 and pump controller 102 other flow control means. Temperature is preferably induced in liquid in pathway 120 by a high heat capacity bath 170 which has high heat transfer and precise temperature control characteristics.

While other media may be used in such a bath, such as oil or high heat capacity fluids, it is preferred to use a precisely specified non-linear heat-sink material such as paraffin, as matter 180 in heating chamber 70. In this case, matter 180 is a stable substance which changes state from a solid to a liquid and maintains a constant desired predetermined temperature during the state change. Particularly suited for use in bath 170 is paraffin. Paraffin may be formulated to accurately and precisely melt at a selected temperature. Such paraffin is currently available from ASTOR Specialty Chemicals, 1600 Commerce, Marshall, Tex. 75670. As an example, matter 180 may be selected to have a melting point of 120° centigrade.

Heating of matter 180 is accomplished by a set of electrical heating elements, generally referenced by 182, which are turned off and on by a bimetallic temperature switch 184. Heating elements 182 are powered by a standard electrical plug assembly 186 which is interconnected to heating elements 182 via electrical lines 183, 185 and 188. Bimetallic temperature switch 184 is interposed between line 183 and line 185. Dashed lines indicate electrical line residence in bath 170.

Switch 184 is selected to open at a temperature which is above the melting point of matter 180 (e.g. 152° centigrade and to close at a temperature (e.g. 148° centigrade) and above the activation temperature of temperature sensing element 160. So constrained, heating of matter 180 is the result of a hysteresis effect of the temperature sensor, making operation temperature stable. Further, it should be noted that, for sterilization purposes, such a 4° temperature differential permits the operating (sterilizing) temperature to be considered substantially constant.

System 10 may be constructed from a large number of parts generally available in commerce today. Examples of parts which may be used are as follows:

| System 10 Part | Commercial Part |
| --- | --- |
| Pump 100 | Flojet Pump model #03655E7011A, available from Flojet, ITT Industries, 201 CON, Fort Hill Ranch, CA. |
| Temp. Sensor Switch 184 | Texas Instruments 20260 bimetal thermal switch, Normally Closed. |
| Temp. Sensor Switch 160 | Texas Instruments 20260 bimeatl thermal switch, Normally Open. |
| Pres. Sensor Switch 150 | Texas Instruments 36PS-50 psi, Normally Open. |

-continued

| System 10 Part | Commercial Part |
| --- | --- |
| Heating Elements 182 | TEMCO Finned Strip Heaters, Type 4, 500 Watt, available from TEMCO, 607 North Central, Wood Dale, IL 60191. |
| Valve 140 | Solenoid Valve #4639K8 (120 volt, .13 Amps), available from McMaster-Carr Supply Co., www.mcmaster.com. |
| Press. Rel. Valve 130 | CA Series In-line Adjustable Relief Valve having a cracking pressure range from 50 to 150 PSIG, available from NUPRO Company, 4800 East 345$^{th}$ Street, Willoughby, OH 44094. |
| Pathway 118 | Preferably constructed from high pressure, stainless steel tubing (with all joints welded to withstand temperatures above melting temperature of matter 180). |

The time to sterilize an item, using saturated steam at a given temperature is well known and summarized in Table 1 below:

TABLE 1

| Time to sterilize | Sterilization temperature |
| --- | --- |
| 20 minutes | 121° Centigrade |
| 10 minutes | 128° Centigrade |
| 3.5 minutes | 134° Centigrade |
| Nearly instantaneous | 141° Centigrade |

However, data in Table 1 is not directly related to SAL's. Therefore, some nominal experimentation may be necessary to develop known sterilization criteria for each system 10. Through experimentation it has been found that water sterilization by system 10 at different parametric levels of flow yields different SAL's for assorted species tested. It should not be surprising that SAL's vary for different microbes and other water-borne organisms.

Figure 2:
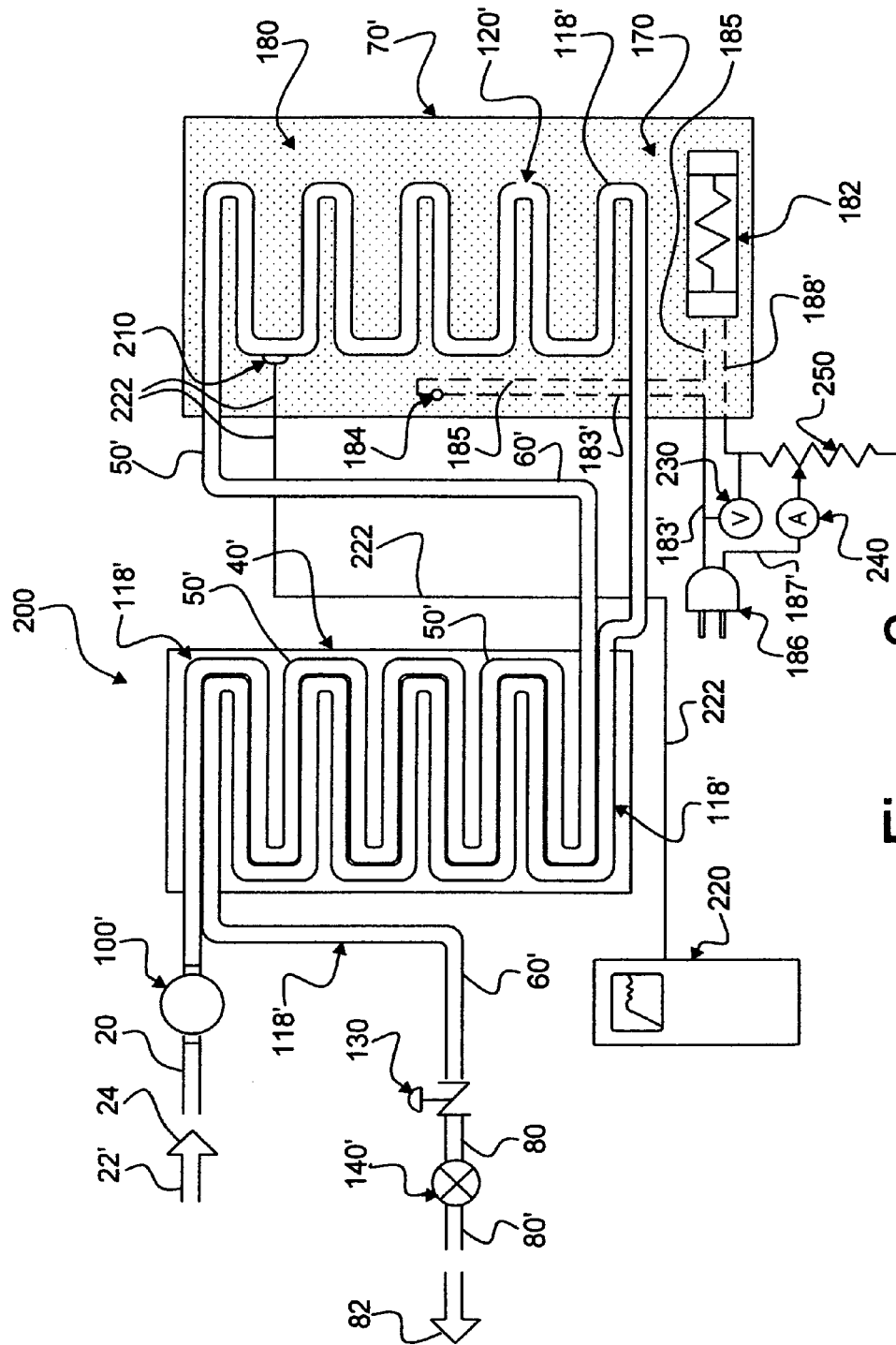
FIG. 2 is a schematic of a test system model used to determine effectiveness of a sterilization process consistent with the instant invention.

FIG. 2 is a schematic representation of a test model 200 used to test effectiveness of sterilizing aqueous solutions by processes consistent with the instant invention. As seen in FIG. 2, model 200 comprises a source 22' of influent contaminated water. In this case, source 22' is a 60 gallon drum strategically disposed above a pump 100' for easy priming.

Similar to system 10 seen in FIG. 1, model 200 comprises an influent channel 20, wherethrough water from a source 22' (see arrow 24) is delivered, a pump 100', a heat exchanger 40' through which influent liquid flows in an input pathway 50' and through which effluent liquid flows in an output pathway 60', a heating chamber 70' and a discharge pathway 80' (see arrow 82).

Pump 100' is manually controllable. Pump 100' has a variable pumping capacity which is manually adjusted to supply a predetermined volume of liquid flow through the system. A needle valve 140' is used for manual control of flow through model 200. Temperature of solution in pathway 120' (which is the in heating bath portion of total system pathway 118') is monitored by means of a temperature sensor 210 (a thermocouple) and a graphic recorder 220. Note that an electrical line 222 interconnects sensor 210 and recorder 220. In this model, an Esterline Angus Video Graphic Model B recorder was used.

Energy supplied to heating elements 182 of heating chamber 70' of model 200 was monitored by a voltmeter 230 and an ammeter 240. Varying amounts of energy was supplied from electrical plug assembly 186 to heating elements 182 and therefrom to bath 170 of heating chamber 70' via a variable voltage rheostat 250. Note that electrical lines 183', 185, 187' and 188' are used to supply electrical energy to heating elements 182. Line 183' interconnects assembly 186 and one side of temperature sensor switch 184. The other side of temperature sensor switch 184 is connected to heaters 182 via electrical line 185. Ammeter 240 is placed in series (via electrical line 187') from plug assembly 186 to rheostat 250. Rheostat 250 is connected to heating elements 182 via electrical line 188'.

Model 200 system liquid pathway 118' was designed to be capable of withstanding any internal pressure generated by heating of liquid within the pathway to temperatures within the scope of reasonable experimental safety limits while constraining liquids in pathway 118' to remain in a liquid state.

In model 200, liquid pathway 118' had a volume of 600 ml. Temperature was held between 143 and 144 degrees centigrade. Pump 100' supplied liquid at a constant pressure of 95 psi. Heat exchanger 40' employed coaxial piping. Pop valve 130 (a pressure release valve) was rated at 50 psi. As earlier disclosed, needle valve 140' was used to manually regulate flow rate through pathway 118'.

Temperature of pathway 118' was manually monitored by thermocouple 210 placed in thermal communication with pathway 118'. As earlier disclosed, an Estiline Angus model videographic system B (recorder 220) was used to continuously monitor temperature. Variations in temperature caused by increasing or decreasing rate of flow were adjusted by rheostat 250 which adjusted electric power supplied to a set of heating elements, generally referenced as 182. In model 200, four such 500 watt heating elements were employed.

Biologic testing was performed to determine effectiveness of sterilization at different flow rates using water contaminated with the following four different microorganisms:
1. *Bacillia sterothermopbilus*
2. *E. coli*
3. *Candida Aldicans*
4. *Pseudomonas aeruginosa*

A predetermined quantity of each microorganism was mixed with 25 gallons of distilled water and dispensed into a drum to provide source 22'. A serial dilution of each batch of microorganisms was titrated and tested to establish the concentration of each organism in the batch. Every batch prepared was determined to contain at least $10^6$ organisms.

Each of the four test organisms were run in duplicate on different days. A test protocol was prepared to run five different effective sterilization periods on each organism. Generally, flow rates employed were divided into a plurality of constant flow one and one-half hour periods. In the runs, flow rates used ranged from 50 to 350 milliliters per minute, in 50 milliliter per minute increments. However, due to lack of meaningful results at lower flow rates and limits on volumes of solution available in model 200, less than a complete complement of flow rates were often used, e.g. 250, 300 and 350 milliliters/minute were used in a test run performed on Apr. 25, 2003, results of which are provided hereafter.

Samples were taken at fifteen minute intervals throughout each test period (providing seven samples per period). Each sample was tested by placing a milliliter aliquot onto a blood agar or enriched agar plate, incubated for 48 hours and read by a qualified microbiologist. As seen by the examples of data provided hereafter, kill ratio of each sample generally exceeded a $10^{-6}$ organism reduction in processed effluent.

Though all tests showed similar sterilization results, a summary of two tests using *bacillia sterothermopbilus* are provided, in Tables 3 and 5 below, as exemplary results of running model 200. Dates of performance of the exemplary tests were Apr. 19, 2003 and Apr. 25, 2003. For each test run, content of source 22' was titrated as a control. Two sets of such results, one set for each solution tested on Apr. 19, 2003 and Apr. 25, 2003, are provided separately in Tables 2 and 4, respectively.

TABLE 2

Titration of Stock Culture Used Apr. 19, 2003
Sample volume is 1.0 ml/each dilution (unless otherwise noted).
Plates incubated @59° C. for 18 hours

| Event | Dilution | Colonies |
|---|---|---|
| 1 | $10^{-1}$ | TNTC** |
| 2 | $10^{-2}$ | TNTC** |
| 3 | $10^{-3}$ | TNTC** |
| 4 | $10^{-4}$ | TNTC** |
| 5 | $10^{-5}$ | no record |
| 6 | $10^{-6}$ | no record |
| 7 | $10^{-7}$ | ~600 |
| 8 | $10^{-8}$ | *** |
| 9 | $10^{-9}$ | *** |
| 10 | $10^{-10}$ | *** |
| 11 | $10^{-0}$* (Stock) | TNTC** |

*0.250 ml sample volume
**Too Numerous To Count
***Titration not performed due to measurable level at event 7

TABLE 3

Test Run Apr. 19, 2003 (Temperature of pathway 118': 143 to 144° C.

| Run # | Flow Rate (ml/min) | Time in minutes (within run) | Colonies |
|---|---|---|---|
| I | 100 | 0 | 2** |
|  |  | 15 | 0 |
|  |  | 30 | 0 |
|  |  | 45 | 0 |
|  |  | 60 | 0 |
|  |  | 75 | 0 |
|  |  | 90 | 0 |
| II | 150 | 0 | 0 |
|  |  | 15 | 0 |
|  |  | 30 | 0 |
|  |  | 45 | 0 |
|  |  | 60 | 0 |
|  |  | 75 | 0 |
|  |  | 90 | 0 |
| III | 200 | 0 | 0 |
|  |  | 15 | 0 |
|  |  | 30 | 0 |
|  |  | 45 | 0 |
|  |  | 60 | 0 |
|  |  | 75 | 0 |
|  |  | 90 | 0 |
| IV | 300 | 0 | 0 |
|  |  | 15 | 0 |
|  |  | 30* | 450 |
|  |  | 45* | 150 |

*See note (reference [*]) following Table 5.
**Initial contamination in effluent pathway.

TABLE 4

Titration of Stock Culture Used Apr. 25, 2003
Sample volume is 1.0 ml/each dilution (unless otherwise noted).
Plates incubated @59° C. for 18 hours

| Event | Dilution | Colonies |
|---|---|---|
| 1 | $10^{-1}$ | TNTC** |
| 2 | $10^{-2}$ | TNTC** |
| 3 | $10^{-3}$ | 1000 |
| 4 | $10^{-4}$ | 400 |

TABLE 4-continued

Titration of Stock Culture Used Apr. 25, 2003
Sample volume is 1.0 ml/each dilution (unless otherwise noted).
Plates incubated @59° C. for 18 hours

| Event | Dilution | Colonies |
|---|---|---|
| 5 | $10^{-5}$ | 250 |
| 6 | $10^{-6}$ | 180 |
| 7 | $10^{-7}$ | 120 |
| 8 | $10^{-8}$ | 75 |
| 9 | $10^{-9}$ | 64 |
| 10 | $10^{-10}$ | 25 |
| 11 | $10^{-0}$* (Stock) | TNTC** |

*0.250 ml sample volume
**Too Numerous To Count

TABLE 5

Test Run Apr. 25, 2003 (Temp. of pathway 118': 143 to 144° C.)

| Run # | Flow Rate (ml/min) | Time in minutes (within run) | Colonies |
|---|---|---|---|
| I | 250 | 0 | 0 |
|  |  | 15 | 0 |
|  |  | 30 | 0 |
|  |  | 45 | 0 |
|  |  | 60 | 0 |
|  |  | 75 | 0 |
|  |  | 90 | 0 |
| II | 300 | 0 | 0 |
|  |  | 15 | 0 |
|  |  | 30 | 0 |
|  |  | 45 | 0 |
|  |  | 60 | 0 |
|  |  | 75 | 0 |
|  |  | 90 | 0 |
| III | 350 | 0 | 0 |
|  |  | 15 | 0 |
|  |  | 30 | 0 |
|  |  | 45 | 0 |
|  |  | 60 | 0 |
|  |  | 75* | 1000 |

*Tank take-off connection at a point 2.5 gallons from tank bottom. Test samples were taken until flow became erratic due to tank drainage. This variation in liquid flow caused heating chamber temperature to first increase rapidly, turning off bimetal over temperature protectors (not otherwise disclosed) resulting in a dramatic decrease in operating temperature. Data at run #III, time 75 minutes (and at run#II, times 30 and 45 minutes) provided to permit a comparative assessment with data derived from system 200 under normal operating conditions.

Results from all tests proved the efficacy of the instant invention. Independent of microorganisms tested and flow rates tested, system model 200 clearly sterilized contaminated influent to produce a continuously flowing sterilized effluent. The effectiveness of sterilization was demonstrated when compared with final samples of contaminated and unsterilized effluent which resulted when temperature of model 200 precipitously declined as an end-of-run phenomenon when water from source 22' was depleted.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method by which a self-regulating and self-interrupting flow through system sterilizes an aqueous liquid influent, contaminated by microbes, received from a contaminated liquid source, to a predetermined SAL without requiring a fluid feedback pathway to a source of aqueous liquid influent, said method comprising the steps of:

providing:

(a) a temperature sensor by which temperature of the influent is measured for the purpose of establishing a valve control signal indicating a predetermined anti-microbial temperature is met;

(b) a pressure sensor by which pressure of the influent is measured for the purpose of establishing a valve control signal indicating a predetermined anti-microbial pressure is met;

(c) only two system external access orifices and an associated conduit for fluid flow, said orifices comprising an input orifice through which contaminated liquid flows from the source and an exit orifice through which decontaminated liquid is dispensed for use;

(d) the conduit comprising a single, closed, unbifurcated flow-through pathway which only communicates with the input orifice on an upstream end and with the exit orifice on a downstream end; and (e) gated valving which normally closes said conduit to flow unless both of said temperature and pressure sensors issue valve control signals indicating that at least established predetermined values of temperature and pressure, respectively, have been met and automatically opens to permit dispensing flow when both valve control signals indicate at least the established predetermined values have been met;

displacing unsterilized influent to fill the conduit which remains closed to delivery of effluent from the exit orifice until both established temperature and pressure of the influent are measured within the conduit;

when and only when valve control signals from both temperature and pressure sensors communicate established predetermined values are measured, automatically initiating internally controlled said gated valving to an open state and displacing, at a preset flow-rate, microbe-containing influent liquid through the closed flow-through pathway, said flow rate being correlated to the established predetermined values of temperature and pressure;

said gated valving being continuously acted upon by said temperature and pressure sensors to impose preset flow permitting conditions upon the liquid influent as it is displaced through the conduit assuring microbes are killed to thereby produce a water based medium comprising living organisms at a predictable SAL while preventing vaporization of the aqueous liquid; and discharging aqueous liquid at the predictable SAL as an effluent from the conduit through the only exit orifice only when preset flow permitting conditions are met.

2. A method by which an influent aqueous liquid from a source of contaminated liquid containing microbes is sterilized to a predetermined SAL in a closed, unbifurcated, self-interrupting, flow through system, without an internal return pathway back to the source, and discharged from the closed system as a sterilized effluent comprising the steps of:

providing a set of system controls comprising:

(a) a temperature sensor which measures temperature of influent to provide a gating signal at a predetermined anti-microbial temperature level;

(b) a pressure sensor which measures pressure of the influent to provide a gating signal at an established pressure level correlated to the predetermined microbial temperature level to assure sterilization to the predetermined SAL;

(c) internally controlled valves which are self-actuated by gating signals from the temperature sensor and pressure sensors to close flow through the system until both the predetermined temperature and established pressure levels are achieved thereby assuring that system contained influent is sterilized to the predetermined SAL and which are automatically opened when both levels are met;

and (d) providing a closed, single, unbifurcated pathway, flow-through system wherein the only source of contamination is the microbe-containing influent aqueous liquid;

internally controlling flow through the system at start-up for complete containment of introduced liquid from the source by preventing of all effluent flow from the system while collectively elevating temperature and pressure conditions within the system to the predetermined temperature and established pressure levels effective for sterilizing the influent aqueous liquid to be free of living organisms to a predetermined SAL;

only when both predetermined temperature and established pressure levels are exceeded within the system, self-actuating valves open flow through the system to permit a predetermined continuous unidirectional flow rate of each unit volume of the aqueous liquid while retaining the necessary temperature and pressure conditions such that the predetermined temperature and established pressure levels within the system are met and each unit volume of aqueous liquid is retained within temperature and pressure conditions for a sufficient period to be sterilized to the predetermined SAL and discharged as such.

* * * * *